(12) United States Patent
Smith

(10) Patent No.: US 6,207,674 B1
(45) Date of Patent: Mar. 27, 2001

(54) DEXTROMETHORPHAN AND OXIDASE INHIBITOR FOR WEANING PATIENTS FROM NARCOTICS AND ANTI-DEPRESSANTS

(76) Inventor: Richard A. Smith, 7569 Cabrillo Ave., La Jolla, CA (US) 92037

( * ) Notice: Subject to any disclaimer, the term of this patent is extended or adjusted under 35 U.S.C. 154(b) by 0 days.

(21) Appl. No.: 09/471,060

(22) Filed: Dec. 22, 1999

(51) Int. Cl.$^7$ ............... A61K 31/44; A61K 31/27; A61K 31/135

(52) U.S. Cl. ............... 514/289; 514/305; 514/491; 514/649; 514/651; 514/652; 514/654

(58) Field of Search ............... 514/289, 305, 514/491, 649, 651, 652, 654

(56) References Cited

U.S. PATENT DOCUMENTS

| | | |
|---|---|---|
| 4,316,888 | 2/1982 | Nelson . |
| 5,166,207 | 11/1992 | Smith . |
| 5,206,248 | 4/1993 | Smith . |
| 5,321,012 | 6/1994 | Mayer et al. . |
| 5,350,756 | 9/1994 | Smith . |
| 5,352,683 | 10/1994 | Mayer et al. . |
| 5,366,980 | 11/1994 | Smith . |
| 5,502,058 | 3/1996 | Mayer et al. . |
| 5,556,838 | 9/1996 | Mayer et al. . |
| 5,863,927 * | 1/1999 | Smith et al. ............... 514/289 |

OTHER PUBLICATIONS

Bisaga, A., et al, "Opiate withdrawal with dextromethorphan [letter]," *Amer. J. Psychiatry 154*: 584 (1997).

Grass, S., et al, "NMDA receptor antagonists potentiate morphine's antinociceptive effect in the rat," *Acta Physiol. Scand. 158*: 269–73 (1996).

Hoffmann, O., et al, "Dextromethorphan potentiates morphine antinociception, but does not reverse tolerance in rats," *Neuroreport 7*: 838–40 (1996).

Kauppila,T., et al, "Dextromethorpan potentiates the effect of morphine in rats with peripheral neuropathy," *Neuroreport 9*: 1071–4 (1998).

Koyuncuoglu, H., et al, "The treatment of heroin addicts with dextromethorphan: a double–blind comparison of dextromethorphan with chlorpromazine," *Int. J. Clin. Pharmacol. Ther. Toxicol. 28*: 147–52 (1990).

Manning, B.H., et al, "Continuous coadministration of dextromethorphan or MK–801 with morphine: attenuation of morphine dependence and naloxone–reversible attenuation of morphine tolerance," *Pain 67*: 79–88 (1996).

Mao, J., et al, "Oral administration of dextromethorphan prevents the development of morphine tolerance and dependence in rats," *Pain 67*: 361–8 (1996).

Plesan, A., et al, "Comparison of ketamine and dextromethorphan in potentiating the antinociceptive effect of morphine in rats," *Anesth. Analg. 86*: 825–9 (1998).

Zhang,Y., et al, "Dextromethorphan: Enhancing its systemic availability by way of low–dose quinidine–mediated inhibition of cytochrome P4502D6," *Clin. Pharmacol. Ther. 51*: 647–655 (1992).

Bisaga et al., Opiate Withdrawal With Dextromethorphan, Am J. Psychiatry, 154:4, p. 584, Apr. 1997.*

Zhang et al., Dextromethorphan: Enhancing its systemic availability by way of low–dose quinidine–mediated inhibition of cytochrome P4502D6, Clin Pharmacol & Therapeutics, 51:6 pp. 647–655, Jun. 1992.*

* cited by examiner

Primary Examiner—Frederick Krass
Assistant Examiner—Donna Jagoe
(74) Attorney, Agent, or Firm—Patrick D. Kelly

(57) ABSTRACT

Patients can be helped to break free of addictive or habit-forming narcotics and anti-depressants, by treatment using two drugs. One drug is dextromethorphan (DM), which has been used for decades as an anti-tussive (cough-suppressing) drug in cough syrups. The other drug is an oxidase inhibitor which suppresses activity of a liver enzyme called cytochrome P450-2D6 (also called debrisoquin hydroxylase, sparteine monooxygenase, cytochrome P450-DB, and CYP2D6). In most patients, this oxidase enzyme rapidly degrades DM and converts it into a metabolite called dextrorphan. An oxidase inhibitor (such as quinidine) which suppresses cytochrome P450-2D6 activity increases the half-life and concentration of DM in the circulating blood. When this combined treatment was administered orally to patients who had become dependent on morphine and anti-depressant drugs because of chronic intractable pain, it initially helped the patients reduce their dosages of morphine and other drugs, including anti-depressants. When additional testing was done, the combined treatment allowed patients to entirely terminate all use of morphine and anti-depressants, with minimal withdrawal or other adverse effects. Importantly, these same patients received no substantial benefit from taking dm by itself, without an oxidase inhibitor. Accordingly, the combination of dextromethorphan plus an anti-oxidase drug can allow at least some patients to break entirely free of narcotics and/or anti-depressants, even after years of use for chronic pain and other medical problems, even when they are not substantially helped by dextromethorphan alone.

20 Claims, No Drawings

DEXTROMETHORPHAN AND OXIDASE INHIBITOR FOR WEANING PATIENTS FROM NARCOTICS AND ANTI-DEPRESSANTS

BACKGROUND OF THE INVENTION

This invention is in the field of pharmacology, and relates to drug treatments for reducing the dependence of patients on habit-forming and potentially addictive drugs, including narcotics and anti-depressants.

The term "narcotic" as used herein has the same meaning used in standard medical reference works, such as the "more recent" definitions used in *Stedman's Medical Dictionary*, 26th edition (Williams & Wilkins Publ., Baltimore, 1995) and in the "Analgesics" chapter in the "Drug Evaluations" subscription service published by the American Medical Association (Chicago). Briefly, "narcotics" as used in any definition (either classical or recent) includes: (1) opiate drugs, defined as any preparation or derivative of opium, a natural mixture derived from poppy plants that includes a number of medically important and/or habit-forming or addictive drugs, including morphine, codeine, noscapine, papaverine, thebaine, and heroin; and, (2) opioid drugs, which includes opiates as well as various synthetic narcotic drugs having similar or related chemical structures and effects. Such synthetic narcotics include meperidine (sold under trademarks such as DEMEROL™), hydrocodone (sold under trademarks such as VICODIN™), hydromorphone (sold under trademarks such as DILAUDID™), propoxyphene (sold under trademarks such as DARVON™), oxycodone (sold under trademarks such as PERCODAN™ when mixed with aspirin, or PERCOCET™ when mixed with acetaminophen), levorphanol, fentanyl, and methadone.

Under a more recent definition that has come to be accepted within the medical profession, the term "narcotics" has been broadened somewhat, to include other synthetic drugs which have "effects that are similar to opium and its derivatives". In order for a drug to be to classified as a "narcotic", its effects must include: (1) the ability to induce "significant alteration of mood and behavior"; (2) the ability to induce a condition of "stuporous analgesia"; and (3) a substantial risk of dependence, tolerance, and/or addiction.

As used herein, the term "narcotic" specifically excludes: (1) barbiturate drugs (which are a separate category of drugs, derived from barbituric acid), even though some barbiturate drugs have many of the same types of effects as narcotics; (2) cocaine and its derivatives, such as crack; and (3) drugs with purely anesthetic or analgesic activity, which do not alter mood or pose a serious risk of addiction and abuse. None of those three categories are relevant to the current invention.

This current invention is limited to methods and compounds for "weaning" a dependent or addicted person from the grip of a habit-forming narcotic drug as defined above (or an anti-depressant drug, as discussed below). This invention involves a drug treatment which can help patients (including patients who have suffered for years from chronic and intractable pain) entirely terminate any subsequent use of a habit-forming narcotic drug.

It is recognized by the Applicant that these same or similar methods and compounds may also be highly useful for helping patients break an addiction to or dependence on barbiturates, cocaine, and certain other addictive or habit-forming drugs which have effects similar to narcotics. Accordingly, the combined drug treatment disclosed herein can and should be evaluated on patients addicted to barbiturates, cocaine, and other addictive drugs. However, the teachings and claims herein do not involve any method of terminating the use of cocaine (or crack, or other cocaine derivatives) or barbiturates, since those two classes of drugs are specifically excluded from the teachings herein.

As is well-known to physicians and other health-care providers, dependence on and addiction to narcotic drugs is a serious and widespread medical and sociological problem. It is also a tragic problem, since most such addictions are triggered not by reckless users who want to get "high" or "stoned". Instead, most people who are addicted to narcotic pain-killers first began using them to help them cope with a serious medical problem that required the use of powerful pain-killing drugs.

As is well-known to physicians and other health-care providers, there is a major need for better methods of helping patients who are "hooked" on narcotics. Currently available methods work some of the times, for some people; however, the struggle to break free of an addiction to, or any long-term use of, a narcotic is a terrible ordeal, even under the best conditions (such as in a professionally-staffed rehabilitation center with full-time living quarters). Although some people manage to break free, usually with the help of on-going support from groups similar to Alcoholics Anonymous, the sad fact is that a majority of all patients who try to break free of a narcotic addiction never fully succeed.

Even among people who are merely "dependent" on narcotics, and who use narcotics to help them cope with chronic severe pain (such as pain caused by cancer or chemotherapy, diabetes, an autoimmune disease, repeated back or neck surgeries, neuropathic or phantom pain, lingering effects of a severe injury or infection, etc.), the side effects caused by narcotics can render life miserable. Such people often must struggle through each day feeling dazed, groggy, and semi-stuporous, as well as frequently nauseous and frequently constipated. They would be extremely relieved and grateful for any treatment that would help them return to a more normal life, where the pain is kept at a tolerably low level while the feelings of dazed grogginess, frequent nausea, constipation, and other side effects of the narcotic are gone.

As used herein, "long-term" use of a narcotic or anti-depressant drug refers to use of such drug by the patient for a sufficiently prolonged period of time to allow the patient to develop a substantial level of dependence on, or addiction to, the narcotic or anti-depressant drug. The method of treatment disclosed herein is designed to help patients break free from such drugs, after they have reached a point where they are unable to stop taking them without substantial medical intervention and assistance.

It is also recognized by the Inventor herein that this same general method (i.e., use of dextromethorphan in conjunction with an oxidase inhibitor) may also be able to help patients avoid the gradual development of dependence on, or addiction to, such habit-forming drugs, when DM plus an oxidase inhibitor are administered in conjunction with an opiate or other narcotic and/or with an anti-depressant, to treat a patient suffering from chronic and intractable pain or another long-term medical problem. Based on various results obtained to date, it is further believed by the Inventor herein that such treatment (i.e., DM plus an oxidase inhibitor in conjunction with a narcotic and/or anti-depressant) is likely to perform better than any and all prior efforts to use dextromethorphan (or other mild NMDA antagonist drugs)

in conjunction with narcotics, to reduce the development of dependence on such narcotics. However, that promising form of treatment has not yet been specifically tested and evaluated, and is not addressed or covered by the claims herein.

Prior Use of Dextromethorphan to Potentiate Opiate Drugs

A substantial number of published reports and patents have stated that dextromethorphan, dextrorphan, and other NMDA antagonist drugs can "potentiate" and increase the potency of opiate drugs such as morphine. Accordingly, these reports indicate that using DM in combination with an opiate drug can reduce the dosage of an opiate drug that is required to achieve a desired level of pain-killing efficacy. Some of these reports also suggest that administering DM or another NMDA antagonist drug along with an opiate drug can also help reduce the likelihood that a patient will develop tolerance, dependence, or addiction to the opiate drug. US patents include U.S. Pat. No. 5,321,012 (Mayer et al 1994), U.S. Pat. No. 5,556,838 (Mayer et al 1996), and U.S. Pat. No. 5,654,281 (Mayer et al 1997). Published articles include Koyuncuoglu et al 1992, Trujillo et al 1994, Elliott et al 1994, Advokat et al 1995, Elliott et al 1995, Grass et al 1996, Mao et al 1996, Manning et al 1996, Hoffmann et al 1996, Kauppila et al 1998, and Plesan et al 1998.

However, it appears that all of the above-cited articles involved efforts to merely reduce the dosages of opiates that were required to obtain a satisfactory level of pain-reducing efficacy. Apparently, none of these articles seriously contemplated or proposed that DM, in combination with an entirely different drug that none of those researchers used or tested, might be able to completely and totally break and terminate a dependent or addicted person's need for opiates.

Based on two small-scale studies on heroin addicts in Turkey, it was reported that DM in combination with other drugs such as tizanidine or diazepam might be useful in treating addicts who were suffering withdrawal symptoms (Koyuncuoglu et al 1990 and 1995). However, those articles and a subsequent published letter (Bisaga et al 1997, which reported essentially the same results) apparently did not generate serious attention among other researchers trying to treat heroin addicts.

Just as importantly, none of the patents or articles cited above taught or suggested, in any way, a combination of dextromethorphan with a cytochrome oxidase inhibitor for weaning people from opiates.

Despite all the ongoing efforts to try to help addicts and others who are dependent on or addicted to opiates and other narcotics, there are no adequate and satisfactory ways under the prior art to help opiate users completely terminate their use of opiates and other habit-forming narcotics. A major and important need still exists for improved methods to help people break completely free of dependence on, or addiction to, habit-forming opiates and other narcotics.

It should also be noted that the Applicant/Inventor herein, Richard Smith, is also the inventor or co-inventor on a number of prior US patents involving a combination of dextromethorphan with an oxidase enzyme inhibitor. Those prior US patents include U.S. Pat. No. 5,166,207 (on treating neurological disorders), U.S. Pat. No. 5,206,248 (on treating emotional lability), U.S. Pat. No. 5,350,756 (on treating intractable coughing), U.S. Pat. No. 5,366,980 (on treating dermatitis), and U.S. Pat. No. 5,863,927 (on treating chronic and intractable pain). Smith's research in this field in conjunction with other collaborators is also described in Zhang et al 1992. However, none of those items relate to or suggest the newly discovered use and treatment disclosed herein.

Accordingly, one object of this invention is to disclose a medical treatment involving a certain type of drug combination which can help people break free of dependence on, or addiction to, habit-forming narcotic drugs, so that affected people (including patients who suffer from chronic pain) can completely terminate their use of narcotic drugs.

During the research which led to this invention, it was also discovered that patients who suffered from chronic intractable pain, and who were able to completely terminate their dependence on pain-killing narcotics using a DM/oxidase inhibitor combination, can also, in at least some cases, break free of anti-depressant drugs as well. Accordingly, another object of this invention is to disclose a medical treatment which can help people terminate long-term use of anti-depressant drugs.

These and other objects of the invention will become more apparent through the following summary and description of the preferred embodiments.

SUMMARY OF THE INVENTION

Patients can be helped to break free of addictive or habit-forming narcotics and anti-depressants, by treatment using two drugs. One drug is dextromethorphan (DM), which has been used for decades as an anti-tussive (cough-suppressing) drug in cough syrups. The other drug is an oxidase inhibitor which suppresses activity of a liver enzyme called cytochrome P450-2D6 (also called debrisoquin hydroxylase, sparteine monooxygenase, cytochrome P450-DB, and CYP2D6). In most patients, this oxidase enzyme rapidly degrades DM and converts it into a metabolite called dextrorphan. An oxidase inhibitor (such as quinidine) which suppresses cytochrome P450-2D6 activity increases the half-life and concentration of DM in the circulating blood. When this combined treatment was administered orally to patients who had become dependent on morphine and anti-depressant drugs because of chronic intractable pain, it initially helped the patients reduce their dosages of morphine and other drugs, including anti-depressants. When additional testing was done, the combined treatment allowed patients to entirely terminate all use of morphine and anti-depressants, with minimal withdrawal or other adverse effects. Importantly, these same patients received no substantial benefit from taking dm by itself, without an oxidase inhibitor. Accordingly, the combination of dextromethorphan plus an anti-oxidase drug can allow at least some patients to break entirely free of narcotics and/or anti-depressants, even after years of use for chronic pain and other medical problems, even when they are not substantially helped by dextromethorphan alone.

DESCRIPTION OF THE PREFERRED EMBODIMENTS

The treatment disclosed herein involves administration (such as by oral ingestion) of a balanced regimen of two drugs. One drug is dextromethorphan (DM), which has been used for decades as an anti-tussive (cough-suppressing) drug, mainly in cough syrups. DM is available from numerous suppliers. University Compounding Pharmacy (San Diego, Calif.) supplied all DM used in the trials below, in powdered form which was loaded into capsules.

The second drug in the combined treatment disclosed herein must inhibit the activity of an enzyme which exists mainly in the liver. This enzyme was initially referred to as debrisoquin hydroxylase, based on the early discovery that it degrades a drug called debrisoquin, which is used to control high blood pressure.

The debrisoquin hydroxylase enzyme belongs to a family of enzymes known as "cytochrome P-450" enzymes (since they absorb light in the 450 nanometer range), or as "cytochrome oxidase" enzymes (since they oxidize a wide range of compounds that do not naturally occur in circulating blood). These enzymes are found at high concentrations in liver cells, and at lower concentrations in other organs and tissues such as the lungs (e.g., Fonne-Pfister et al 1988). By oxidizing lipophilic compounds, which makes them more water-soluble, cytochrome oxidase enzymes help the body eliminate (via urine, or in aerosols exhaled out of the lungs) compounds that might otherwise act as toxins or accumulate to undesired levels. Since the debrisoquin hydroxylase enzyme fell within the cytochrome P-450 class of enzymes, it was referred as "cytochrome P450-DB", where "DB" referred to debrisoquin.

Some years later, other researchers discovered that a certain oxygenase enzyme in liver tissues degrades an entirely different drug called sparteine. They called that enzyme sparteine monooxygenase. It wasn't until later that researchers realized that debrisoquin hydroxylase and sparteine monooxygenase apparently are the same enzyme.

Still later, as other researchers began trying to organize the complex and overlapping set of cytochrome oxidase enzymes into a logical system of names, they began referring to the debrisoquin hydroxylase/sparteine monooxygenase enzyme as the cytochrome P450-2D6 enzyme. In addition, in some recent articles, the cytochrome P450-2D6 name is abbreviated as "CYP2D6".

Accordingly, this same enzyme has been referred to by at least five different names: debrisoquin hydroxylase, cytochrome P450-DB, sparteine monooxygenase, cytochrome P450-2D6, and CYP2D6.

Since the cytochrome P450-2D6 name appears to have become the predominant and systematized name in recent published reports, that enzyme is referred to herein as cytochrome P450-2D6 (or simply as P450-2D6, for convenience).

In a "normal" and healthy person who has not been treated with an oxidase inhibitor drug, the P450-2D6 enzyme rapidly degrades dextromethorphan, converting it into a similar but altered compound called dextrorphan. However, certain drugs are known which can inhibit the activity of the P450-2D6 enzyme. If a patient is treated with one of these oxidase inhibitor drugs, it will substantially increase the half-life, and the concentration, of DM in the circulating blood of the patient.

One potent oxygenase inhibitor drug is called quinidine, which is a dextrorotatory stereoisomer of quinine. Quinidine normally is used to treat cardiac arrhythmias. Inaba et al 1986 and Nielsen et al 1990 discuss the ability of quinidine to inhibit the oxidation of sparteine in in vivo animal tests. Brinn et al 1986, Brosen et al 1987, and Broly et al 1989 discuss the ability of quinidine to inhibit the degradation of DM by the P450-2D6 enzyme, in liver cell preparations.

Various other drugs are also known to be inhibitors of the P450-2D6 enzyme; a fairly extensive list is provided in Inaba et al 1985. Since quinidine is not tolerated well by everyone, and since quinidine should never be given to anyone who has a heart condition known as a "prolonged QT interval", these other drugs may be of interest to some doctors and their patients. The more potent inhibitors include yohimbine, haloperidol, ajmaline, lobeline, pipamperone, and fluoxetine. Still other drugs that have less potent yet still significant oxidase inhibiting activity include labetalol, chlorpromazine, domperidone, nortriptyline, quinine, oxprenolol, propranolol, timolol, metaprolol, diphenhydramine, papaverine, and mexiletine.

Since people have major variations in their oxidative enzyme activities, screening tests can be undertaken under the supervision of a physician to select a preferred antioxidant for any specific patient. The preferred dosage of any such drug, if it is being used to inhibit the P450-2D6 enzyme in order to boost the levels of DM in a patient who is trying to terminate dependence on a narcotic or anti-depressant, can be determined through trial-and-error tests (more accurately described as "trial-and-adjustment" tests). In this procedure, a patient is prescribed an initial dosage of DM without an oxidase inhibitor, to establish certain baseline values, to ensure that the patient has a properly functioning set of cytochrome enzymes and is not a "poor metabolizer", and to ensure that the patient does not suffer an adverse reaction to the DM. After that baseline test has been completed, the patient is also given a very low "starting" dosage of the oxidase inhibitor or a "best guess" oxidase inhibitor dosage, for a period such as one or two weeks. At the end of that trial period, the patient's sense of well-being is evaluated, along with his/her ability to continue reducing the dosage of the habit-forming narcotic drug to progressively lower levels without suffering from unacceptable levels of pain. In addition, a blood test can be taken to evaluate the concentration of DM in the blood, in the presence of the oxidase inhibitor that is being tested during that time period. Based on the patient's oral report, and the result of any such blood test, the dosage of either or both of the two drugs (DM and the oxidase inhibitor) can be adjusted for the next 1 or 2 week trial period.

Since at least three different drugs will be involved (the habit-forming narcotic drug, the DM, and the oxidase inhibitor), and since the goal of this treatment is to progressively reduce and then completely eliminate the dosage of the habit-forming narcotic drug, this treatment method involves an on-going procedure of weekly, biweekly, or monthly adjustments, wherein a trained physician can adjust the dosage of any or all of the three relevant drugs after each periodic evaluation. Therefore, this process can be regarded as a "weaning" process, since the patient is being weaned (i.e., gradually but entirely removed) from the habit-forming narcotic drug, with the assistance of both (i) dextromethorphan, as an "opiate substitute" drug, and (ii) an oxidase inhibitor, which is administered in order to increase and sustain relatively high concentrations of DM in the circulating blood of the patient.

It should also be recognized that a potent oxidase inhibitor such as quinidine (or even a less potent oxidase inhibitor, at a relatively high dosage) can convert a patient into a "poor metabolizer", as described in articles such as Guttendorf et al 1988, Kupfer et al 1984, and Koppel et al 1987. A small yet significant fraction of the population (roughly 7 to 10 percent of adult Caucasians) has relatively low natural levels of the P450-2D6 enzyme, because of genetic factors. Such people are regarded by the medical profession as somewhat high-risk patients; they must be treated with extra care and attention, since they may be overly sensitive to certain drugs, compared to people with a full set of cytochrome P450 enzymes (usually referred to as "extensive metabolizers" or "good metabolizers"). Dextromethorphan is often used as a test drug, to determine whether a certain patient is an "extensive metabolizer" (with a full set of cytochrome P450 enzymes) or a "poor metabolizer" (with a deficiency in his or her ability to metabolize and eliminate various drugs and potential toxins). Accordingly, if a patient is administered an oxidase inhibitor compound such as quinidine, in a deliberate effort to inactivate that patient's debrisoquin hydroxylase enzyme, the patient should be advised to try to reduce his/her intake of potential toxins, including tobacco products and alcohol.

The combined DM-plus-inhibitor treatment was first tried on a patient who arrived at the offices of the Inventor herein, Dr. Richard Smith, a neurologist who is the founder and Director of the Center for Neurologic Study, in La Jolla, Calif. The patient, who is described in further detail in Example 1, was badly depressed, after having been on narcotic drugs for several years to treat peripheral neuropathy, which caused a burning sensation in her hands and feet, and which had appeared spontaneously with no known cause. She had been to pain management and other medical specialists at the Scripps Institute in La Jolla, but the best treatment they could give her was to place her on a combination of a narcotic pain-killer (morphine sulfate), and two anti-depressants (WELLBUTRIN™ and ELAVIL™). Accordingly, about 5 years after she first began to experience the burning pain in her hands and feet, and after years of taking morphine and anti-depressant drugs, she was referred to the Center for Neurologic Study for a complete neurological evaluation.

A complete physical and neurological exam discovered nothing noteworthy that had not already been observed by her previous doctors. However, Dr. Richard Smith (the Inventor herein) was aware of two things as he was examining and treating her. First, he had seen published reports indicating that if DM was combined with morphine, it could potentiate the pain-relieving effects of morphine in at least some patients, allowing such patients to use lower dosages of morphine to achieve the necessary level of pain relief. Second, he was also aware, from his own previous work, that administering quinidine along with DM can increase the level of DM in the blood of most patients. Accordingly, he suggested that she might want to try DM initially, along with the morphine, and a DM/quinidine combination later.

During her first DM trial period, Dr. Smith did not prescribe quinidine, since he wanted to evaluate the effects of DM alone, without any potential complications from quinidine. She took capsules with 30 milligrams of DM, twice each day.

The results during that initial 3-week trial were unremarkable. In a follow-up exam, the patient reported that her symptoms were unchanged. Although she had slightly decreased the dose of one of the anti-depressant drugs, her use and dosage of morphine and the other anti-depressant remained the same.

After that follow-up exam, Dr. Smith prescribed a combination of DM (30 mg) and quinidine (75 mg), packaged together in single capsules, which she was instructed to take twice a day.

The results of that treatment were indeed remarkable, and the patient began to note considerable relief from her daily pain, and as her improvement continued, she gradually terminated both the anti-depressants and the morphine.

She initially withdrew from the anti-depressants, and began to cut apart each of the pills she targeted for elimination. Initially, she took what she estimated to be 75% of the prescribed dose; then she began taking successively smaller portions of the dissected tablets.

She completely discontinued each drug over a span of ten days, by gradually reducing her daily dose until she was down to "just a crumb". When she had completely eliminated a drug, she made no other changes and went through a stabilization period for a week before she began to reduce her dosage of another medication.

The withdrawal from morphine took place a few weeks after she had stopped the anti-depressants, and she reported that it was more difficult. She attempted it in generally the same manner, by cutting apart the morphine tablets and taking progressively smaller portions. On the days when she was on "her last crumbs", and during the next week, she experienced withdrawal symptoms, including sweating, agitation, and diarrhea. However, those symptoms subsided after she had been free of morphine for a week.

When seen in a follow-up exam, she reported that her pain was much better controlled by the DM/quinidine combination than it had been using a combination of other morphine and anti-depressants, or by any other combination of medications she had been prescribed since her onset of peripheral neuropathy, years earlier. Just as importantly, she felt much more mentally alert and responsive, and more able to carry out and enjoy the normal activities of daily life. She reported that she was keeping her house cleaner than she had felt able to while on morphine and the other drugs, and that her interactions with her family members had improved greatly. As of this writing, she has not requested any further prescriptions for any morphine or other narcotic.

That was the first example observed by Dr. Smith of a patient who completely eliminated his or her dependence on a habit-forming narcotic drug, after being placed on the DM/Q combined treatment regimen. After observing that example, he subsequently performed the same type of treatment on another patient, who responded in essentially the same way, as described in Example 2.

Due to small sample size, these examples are not yet suitable for statistical analysis. Nevertheless, these examples clearly demonstrate that a DM/oxidase inhibitor combination can help at least some patients completely terminate all use of anti-depressants and habit-forming narcotic drugs, even after using anti-depressants and narcotics for years to deal with long-term chronic pain.

Accordingly, this invention involves a drug treatment which uses DM in combination with an oxidase inhibitor drug, to help "wean" patients from dependence on, or addiction to, a habit-forming narcotic drug and/or an anti-depressant.

As used herein, "wean" refers to a process that leads to complete termination of a habit-forming narcotic or anti-depressant drug. This invention does not claim methods of merely reducing dosages of habit-forming drugs that continue to be taken by a patient; instead, it relates to a way to help a dependent or addicted person break entirely free of the dependence or addiction.

Candidate Oxidase Inhibitors

The term "oxidase inhibitor" as used herein refers to a pharmacologically acceptable drug which substantially inhibits a cytochrome oxidase enzyme which rapidly degrades dextromethorphan into its metabolite dextrorphan. That enzyme has been referred to by various researchers as debrisoquin hydroxylase, sparteine monooxygenase, cytochrome P450-DB, and cytochrome P450-2D6. Oxidase inhibitor drugs which are known to inhibit that enzyme include but are not limited to quinidine, quinine, yohimbine, fluoxetine, haloperidol, ajmaline, lobeline, and pipamperone.

Quinidine is highly potent in inhibiting the cytochrome P450-2D6 enzyme; its reported Michaelis-Menton inhibition (Ki) value is quite low, at 0.06 (Inaba et al 1985). A low Ki value indicates high potency, since it indicates that a low concentration of the drug can cause a 50% reduction of the enzyme's activity in an in vitro test.

The next cluster of drugs (in terms of potency ranking) listed in Inaba et al 1985 include yohimbine (Ki=0.33), haloperidol (Ki=1), ajmaline and lobeline (both Ki=2), and pipamperone (Ki=4).

Other drugs with somewhat lower yet still significant abilities to inhibit the P450-2D6 enzyme include labetalol and chlorpromazine (Ki=7 for each), domperidone (Ki=8), nortriptyline, quinine, oxprenolol and propranolol (Ki=15 for each), timolol and metaprolol (Ki=18 for each), diphenhydramine (Ki=20), papaverine (Ki=25), and mexiletine (Ki=30). Fluoxetine was not tested by Inaba et al, but it was subsequently discovered to increase the concentrations of DM in a patient who was taking PROZAC™; this was subsequently confirmed by Otten et al 1993.

Preferably, in order to be useful as disclosed herein with optimal efficacy, an oxidase inhibitor selected for this use should have an inhibitory potency (which can be measured using liver cell preparations, or by measuring levels of DM in blood or urine from a particular patient) which is comparable to or higher than the oxidase inhibiting potency of fluoxetine. If desired, two or more oxidase inhibitors can be used in combination.

It is worth noting that a number of the known oxidase inhibitors have their own neuroactive properties; for example, fluoxetine is better known by its trademark name, PROZAC™. It is widely used as an anti-depressant because of its ability to increase levels of serotonin in body fluids. Accordingly, it may well be useful, in a patient trying to wean himself or herself from a habit-forming narcotic, as both (i) an oxidase inhibitor which can boost and prolong DM levels in the blood, and (ii) as an anti-depressant which can enhance and improve the patient's sense of well-being during a difficult and trying time.

Similarly, the drug haloperidol (better known by its trademark, HALDOL™) helps calm and modulate the nervous system, as evidenced by the fact that it is both an anti-dyskinetic and anti-psychotic drug. As such, it may be useful as a bifunctional oxidase inhibitor in combination with DM, in someone who is going through the struggle of narcotic withdrawal.

Diphenhydramine (one of the lesser-yet-significant oxidase inhibitors) is also potentially significant, since it is an anti-cholinergic agent; as such, it exerts a general calming effect on the nervous system, and it is the active agent in a widely used type of sleeping pill. Accordingly, it may offer a good anti-oxidase drug to be taken at bedtime, both as a sleeping aid and to minimize early-morning pain, which is fairly common among people who use habit-forming narcotics.

Yohimbine is a curious agent; it dilates pupils, and suppresses activity at alpha-adrenergic receptors in the nervous system. Since the alpha-adrenergic system generally inhibits neuronal firing, yohimbine can increase levels of neuronal activity, including neuronal activity involved in sexual excitation and response. As such, yohimbine has been used as an aphrodisiac by humans (although such use is not formally recognized or approved by agencies such as the U.S. Food and Drug Administration), and by livestock breeders and other animal breeders. Accordingly, if a patient's marital relations have suffered due to a narcotic dependency or addiction, or if a patient seems depressed and reports a lack of interest in sex (these are common side-effects of narcotic usage), yohimbine may offer a potentially useful bifunctional agent, for testing in combination with DM. In at least some patients, it may help increase a sense of happiness and well-being that is supported and promoted by satisfactory sexual relations, during the period while a patient is struggling to break free from a narcotic dependency.

The preferred method of administering both the DM and the oxidase inhibitor drug is by oral ingestion of convenient unit-dosage pills, such as capsules or tablets. Alternate forms of oral administration can be used if desired, such as syrups or other liquids, lozenges, troches, etc.

In one preferred mode, a patient can take an oxidase inhibitor about 30 to 45 minutes before taking the DM. This delay between the two dosages will give the oxidase inhibitor drug a period of time to effectively inhibit the debrisoquin hydroxylase enzyme, before that enzyme can degrade any of the DM.

In an alternate preferred mode which is more convenient, a patient can take a single tablet, capsule, or other unit-dosage formulation which contains both the oxidase inhibitor.

If desired, the DM and/or the oxidase inhibitor can be contained in microencapsulated form, which can provide sustained release of either or both compounds.

EXAMPLES

Example 1

Patient Number 1

A female patient, in her 40's and in generally good physical condition, was referred by her prior physician to the Inventor herein, Dr. Richard Smith. She had begun taking narcotic drugs about 5 years earlier, to treat an apparent case of peripheral neuropathy with no known causative event, which presented as a severe burning sensation in her hands and feet. She had been to pain management and other medical specialists, including specialists at the Scripps Institute in La Jolla, but the best treatment they could give her was to place her on a narcotic pain-killer, morphine sulfate, and NEURONTIN™, an anti-convulsant drug which is also used to treat neuropathic pain. She was also taking two anti-depressant drugs, WELLBUTRIN™ and ELAVIL™, to help her cope with depression caused by the combination of (i) a serious physical ailment that had lasted for years with no improvement, and (ii) her dislike of the various side effects of chronically having to take narcotic drugs.

Since she was unhappy with her medical condition and with the side effects of her drug regimen, she was referred to Dr. Smith, a neurological specialist at the Center for Neurologic Study in La Jolla, California, for a complete neurological evaluation.

Dr. Smith gave her a complete physical and neurological examination, which revealed nothing noteworthy that had not already been observed by her previous doctors. However, he was aware of two things which became relevant over the course of her treatment. First, he had seen published reports indicating that in some patients, when DM was combined with morphine, the DM apparently potentiated the pain-relieving activity of morphine, allowing patients to use lower dosages of morphine to achieve a desired level of pain relief. Second, he was also aware, from his own previous work, that co-administering quinidine along with DM can increase the level of DM in the blood of most patients.

Accordingly, since he was unable to recommend anything else that would be likely to provide better results than the narcotics and anti-depressants she was already taking, he suggested that she might want to try DM by itself initially, and possibly the DM/quinidine combination, later.

During her first DM trial period, Dr. Smith did not prescribe quinidine, since he wanted to evaluate the effects of DM alone, without any potential complications from quinidine. She took capsules with 30 milligrams of DM, twice each day.

The results were unremarkable. In a follow-up exam about three weeks later, the patient reported that her symptoms were unchanged. Although she had slightly decreased the dose of one of her anti-depressant drugs, reducing her nighttime dosage of ELAVIL from 250 mg to 100 mg, her use and dosages of morphine and WELLBUTRIN remained the same. She did not feel that the DM treatment had made any major difference in her life.

After that follow-up exam, Dr. Smith prescribed a combination of DM (30 mg) and quinidine (75 mg), packaged together in single capsules, which she was instructed to take twice a day.

The results from the combined DM/quinidine treatment were remarkable, and had a major effect on the patient. She initially began to notice substantially better relief from her daily pain than she had ever noticed from any previous drug treatment. As that process continued, she decided to try to withdraw gradually from her other medications. She initially withdrew from the anti-depressants before attempting to discontinue morphine, and began to cut apart each of the anti-depressants pills she targeted for elimination, initially taking what she estimated to be 75% percent of the prescribed dose, and then successively smaller portions of the dissected tablets. She took about 10 days to gradually decrease and then discontinue each drug, reducing her daily dose, incrementally, until she was down to "just a crumb" of that drug. When she had completely eliminated a drug, she made no other changes and went through a stabilization period for a week before she began eliminating another medication.

In a subsequent follow-up examination, she said she initially felt "speedy" and somewhat jittery after withdrawal of ELAVI® and WELLBUTRIN®, but those problems gradually subsided. After she had completely withdrawn from NEURONTIN™, she reported that she had gained a substantially higher level of mental alertness and acuity; as she described it, she felt as though she had "regained a piece of her brain."

The withdrawal from morphine took place a few weeks after the others, and she reported that it was more difficult. She attempted it in generally the same manner as the anti-depressants, by cutting apart the tablets and taking progressively smaller portions. On the days when she had reduced her dosage to "the last crumbs" of the tablets, and during the week after that, she experienced some withdrawal symptoms, including sweating, agitation, and diarrhea. However, those symptoms subsided after she had been free of morphine for about a week, and she regarded those transient problems as entirely bearable, and certainly worthwhile, since they allowed her to completely eliminate her morphine dependence.

When seen in a follow-up exam, she reported that her pain was better controlled by the DM/quinidine combination than it had been while using morphine and anti-depressants, or any other combination of medications she had been prescribed since her peripheral neuropathy had begun, years earlier. Just as importantly, she felt much more mentally alert and responsive, and more able to carry out and enjoy the normal activities of daily life. She reported that she was keeping her house cleaner than she had been able to, while on morphine and the other drugs, and that her interactions with her family members had improved greatly. As of this writing, she has not requested any further prescriptions for any morphine or other narcotic.

After her transition period was over and she was no longer taking any morphine, she continued to take the DM/quinidine combination. She reported that although she still felt some pain in her feet (especially in the early mornings, before she took her DM/Q capsule), the DM/Q gave her better pain relief than she had ever enjoyed under any other medication.

Example 2

Patient Number 2

After observing the success of the patient described above, the Inventor herein prescribed a similar treatment for another female patient, in her 50's. She suffered from a number of medical problems, including arthritis and excess weight, and in 1996 had fallen, leading to serious bruising of a leg and shoulder. Instead of gradually improving, her condition deteriorated, resulting eventually in knee surgery and neuropathic pain in her feet and legs. By January 1997, she was taking or had recently taken a wide variety of narcotic, anti-depressant, and other drugs, including but not limited to compazine, morphine, VICODIN, LORIBID, NEURONTIN, VALIUM, lorazepam, LORTAB, NORCO, PERCOCET, and PERCOGESIC, at relatively large and frequent dosages (such as 10 tablets per day of VICODIN). These drugs severely impaired her memory and other mental functions, and she had serious trouble walking or doing any other normal activities. In 1998, she was referred to the Center for Neurologic Study.

In the fall of 1998, the patient began DM/quinidine treatment, and for a while she gradually improved. However, in January 1999, she suffered an apparent set of compression fractures resulting in several broken ribs, with no apparent traumatic cause. The pain that resulted drove her back to heavy narcotic usage for several months, to a point where Dr. Smith recommended, in April 1999, that she enter a drug rehabilitation program on an outpatient basis, to try to cut down on her use of and dependence on narcotic drugs. Her marriage by this time was under severe strain, and she was on the verge of giving up and collapsing into a state of complete helplessness.

Instead of entering a drug rehab program, she resolved to try to take control of her life again, and commenced the DM/quinidine program once again with a renewed sense of purpose. Supported and bolstered by Dr. Smith's description of the female patient described above, who had completely terminated all anti-depressants and morphine while on the DM/quinidine treatment, the second patient resolved to take the same approach, and began weaning herself from the anti-depressants and narcotics.

Within roughly three months, by gradually decreasing the dosage of one drug at a time and relying instead on the 30/75 mg combination of DM/quinidine, at a dosage rate of two capsules per day, for her primary pain relief needs, she completely terminated her use of all anti-depressants, and of all narcotics. The only other pain-killer she took was ULTRAM (tramadol), in 50 mg tablets, normally twice a day but with permission to take up to 4 tablets per day as needed. ULTRAM is an analgesic, but it is not an opiate or opioid, and it is not regarded as a narcotic by pharmacists.

While taking that treatment regimen beginning in April 1999, she also lost about 40 pounds, and began carrying out other normal activities, such as gardening, which had been totally beyond her capability previously. She is extraordinarily pleased with the results of the DM/quinidine treatment, and is convinced that it helped her break free of narcotics and effectively gave a decent quality of life back to her.

Thus, there has been shown and described a new and useful means for using a combination of dextromethorphan and an oxidase enzyme inhibitor drug to help patients completely terminate and break free of dependence on or addiction to habit-forming narcotics and/or anti-depressant. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Advokat, C., et al, "Potentiation of morphine-induced antinociception in acute spinal rats by the NMDA antagonist dextrorphan," *Brain Res.* 699: 157–60 (1995)

Bisaga, A., et al, "Opiate withdrawal with dextromethorphan [letter]," *Amer. J. Psychiatry* 154: 584 (1997)

Brinn, R., et al, "Sparteine oxidation is practically abolished in quinidine-treated patients," *Br. J. Clin. Pharmacol.* 22: 194–197 (1986)

Broly, F., et al, "Effect of quinidine on the dextromethorphan O-methylase activity of microsomal fractions from human liver," *Br. J. Clin. Pharmacol.* 28: 29–36 (1989)

Broly, F., et al, "Inhibitory studies of mexiletine and dextromethorphan oxidation in human liver microsomes," *Biochem. Pharmacol.* 39: 1045–1053 (1990)

Brosen, K., et al, "Extensive metabolizers of debrisoquin become poor metabolizers during quinidine treatment," *Pharmacol. Toxicol.* 60: 312–314 (1987)

Elliott, K., et al, "Dextromethorphan attenuates and reverses analgesic tolerance to morphine," *Pain* 59: 361–8 (1994)

Elliott, K., et al, "NMDA receptors, mu and kappa opioid tolerance, and perspectives on new analgesic drug development," *Neuropsychopharmacology* 13: 347–56 (1995)

Fonne-Pfister, R. and Meyer, U., "Xenobiotic and endobiotic inhibitors of cytochrome P-450db1 function, the target of the debrisoquin/sparteine type polymorphism," *Biochem. Pharmacol.* 37: 3829–3835 (1988)

Grass, S., et al, "NMDA receptor antagonists potentiate morphine's antinociceptive effect in the rat," *Acta Physiol. Scand.* 158: 269–73 (1996)

Guttendorf, R. J., et al, "Simplified phenotyping with dextromethorphan by thin-layer chromatography: Application to clinical laboratory screening for deficiencies in oxidative drug metabolism," *Ther. Drug. Monit.* 10: 490–498 (1988)

Hoffmann, O., et al, "Dextromethorphan potentiates morphine antinociception, but does not reverse tolerance in rats," *Neuroreport* 7: 838–40 (1996)

Inaba, T., et al, "In vitro inhibition studies of two isozymes of human liver cytochrome P-450," *Drug Metabolism and Disposition* 13: 443–447 (1985)

Inaba, T., et al, "Quinidine: Potent inhibition of sparteine and debrisoquin oxidation in vivo," *Br. J. Clin. Pharmacol.* 22: 199–200 (1986)

Kauppila T., et al, "Dextromethorphan potentiates the effect of morphine in rats with peripheral neuropathy," *Neuroreport* 9: 1071–4 (1998)

Koppel, C., et al, "Urinary metabolism of dextromethorphan in man," *Arzneim.-Forsch./Drug Research* 37: 1304–1306 (1987)

Koyuncuoglu, H., et al, "The treatment of heroin addicts with dextromethorphan: a double-blind comparison of dextromethorphan with chlorpromazine," *Int. J. Clin. Pharmacol. Ther. Toxicol.* 28: 147–52 (1990)

Koyuncuoglu, H., et al, "Effects of MK 801 on morphine physical dependence: attenuation and intensification," *Pharmacol. Biochem. Behav.* 43: 487–90 (1992)

Koyuncuoglu, H., "The combination of tizanidine markedly improves the treatment with dextromethorphan of heroin addicted outpatients," *Int. J. Clin. Pharmacol. Ther.* 33: 13–9 (1995)

Kupfer, A., et al, "Dextromethorphan as a safe probe for debrisoquin hydroxylation polymorphism," *Lancet ii:* 517–518 (1984)

Manning, B. H., et al, "Continuous co-administration of dextromethorphan or MK-801 with morphine: attenuation of morphine dependence and naloxone-reversible attenuation of morphine tolerance," *Pain* 67: 79–88 (1996)

Mao, J., et al, "Oral administration of dextromethorphan prevents the development of morphine tolerance and dependence in rats," *Pain* 67: 361–8 (1996)

Nielsen, M. D., et al, "A dose-effect study of the in vivo inhibitory effect of quinidine on sparteine oxidation in man," *Br. J. Clin. Pharmacol.* 29: 299–304 (1990)

Plesan, A., et al, "Comparison of ketamine and dextromethorphan in potentiating the antinociceptive effect of morphine in rats," *Anesth. Analg.* 86: 825–9 (1998)

Trujillo, K. A., et al, "Inhibition of opiate tolerance by non-competitive NMDA receptor antagonists," *Brain Res.* 633: 178–88 (1994)

Zhang, Y., et al, "Dextromethorphan: Enhancing its systemic availability by way of low-dose quinidine-mediated inhibition of cytochrome P4502D6," *Clin. Pharmacol. Ther.* 51: 647–655 (1992)

What is claimed is:

1. A method of weaning a patient from long-term use of a habit-forming narcotic drug, comprising administering to the patient a combination of dextromethorphan and a second drug which suppresses oxidation of dextromethorphan by cytochrome oxidase enzyme P450-2D6, wherein:

a. the second drug is administered at an effective concentration which increases measurable levels of dextromethorphan in the patient's blood;

b. the dextromethorphan is administered at a therapeutically effective concentration which, when coadministered with the second drug, allows the patient to reduce his or her dosage of a habit-forming narcotic drug, without intolerable adverse effects, during a gradual weaning process; and, c. the dextromethorphan and the second drug are co-administered to the patient in a manner which allows the patient to decrease and then stop taking the habit-forming narcotic drug without suffering intolerable adverse effects.

2. The method of claim 1 wherein the second drug is quinidine.

3. The method of claim 1 wherein the second drug is selected from the group consisting of yohimbine, haloperidol, ajmaline, lobeline, pipamperone, and fluoxetine, and salts and isomers thereof.

4. The method of claim 1 wherein the second drug is selected from the group consisting of labetalol, chlorpromazine, domperidone, nortriptyline, quinine, oxprenolol, propranolol, timolol, metaprolol, diphenhydramine, papaverine, and mexiletine, and salts and isomers thereof.

5. A method of helping a patient terminate use of a habit-forming narcotic drug, comprising administering, to a patient suffering from dependence on a habit-forming narcotic drug, a combination of dextromethorphan and a cytochrome oxidase inhibitor drug, wherein:

a. the cytochrome oxidase inhibitor drug is effective in increasing measurable levels of dextromethorphan in the patient's blood;

b. the dextromethorphan is administered at a therapeutically effective concentration which, in conjunction with the oxidase inhibitor, allows the patient to reduce and terminate use of the habit-forming narcotic drug, without intolerable adverse effects.

6. The method of claim 5 wherein the second drug is quinidine.

7. The method of claim 5 wherein the second drug is selected from the group consisting of yohimbine, haloperidol, ajmaline, lobeline, pipamperone, and fluoxetine, and salts and isomers thereof.

8. The method of claim 5 wherein the second drug is selected from the group consisting of labetalol, chlorpromazine, domperidone, nortriptyline, quinine, oxprenolol, propranolol, timolol, metaprolol, diphenhydramine, papaverine, and mexiletine, and salts and isomers thereof.

9. A method of weaning a patient from long-term use of a habit-forming narcotic drug, comprising administering to the patient a combination of dextromethorphan and an oxidase inhibitor drug which suppresses oxidation of dextromethorphan by cytochrome oxidase enzyme P450-2D6, wherein:

a. the oxidase inhibitor drug is administered at a concentration which increases dextromethorphan levels in the patient's blood;

b. the dextromethorphan is administered at a concentration which, when coadministered with the oxidase inhibitor drug, allows the patient to terminate administration of a habit-forming narcotic drug without suffering intolerable adverse effects; and, c. the dextromethorphan and the second drug are co-administered to the patient in a manner which allows the patient to terminate administration of the habit-forming narcotic drug.

10. The method of claim 9 wherein the oxidase inhibitor drug is quinidine.

11. The method of claim 9 wherein the oxidase inhibitor drug is selected from the group consisting of yohimbine, haloperidol, ajmaline, lobeline, pipamperone, and fluoxetine, and salts and isomers thereof.

12. The method of claim 9 wherein the oxidase inhibitor drug is selected from the group consisting of labetalol, chlorpromazine, domperidone, nortriptyline, quinine, oxprenolol, propranolol, timolol, metaprolol, diphenhydramine, papaverine, and mexiletine, and salts and isomers thereof.

13. A method of weaning a patient who suffers from chronic pain from long-term use of at least one anti-depressant drug, comprising administering to such patient a combination of dextromethorphan and a second drug which suppresses oxidation of dextromethorphan by cytochrome oxidase enzyme P450-2D6, wherein:

a. the second drug is administered at an effective concentration which increases measurable levels of dextromethorphan in the patient's blood;

b. the dextromethorphan is administered at a therapeutically effective concentration which, when coadministered with the second drug, allows the patient to eliminate use of at least one anti-depressant drug.

14. The method of claim 13 wherein the second drug is quinidine.

15. The method of claim 13 wherein the second drug is selected from the group consisting of yohimbine, haloperidol, ajmaline, lobeline, and pipamperone, and salts and isomers thereof.

16. The method of claim 13 wherein the oxidase inhibitor drug is selected from the group consisting of labetalol, chlorpromazine, domperidone, quinine, oxprenolol, propranolol, timolol, metaprolol, diphenhydramine, papaverine, and mexiletine, and salts and isomers thereof.

17. A method of weaning a patient from long-term use of an anti-depressant drug, comprising administering to such patient a combination of dextromethorphan and a second drug which suppresses oxidation of dextromethorphan by cytochrome oxidase enzyme P450-2D6, wherein:

a. the second drug is administered at an effective concentration which increases measurable levels of dextromethorphan in the patient's blood;

b. the dextromethorphan is administered at a therapeutically effective concentration which, when coadministered with the second drug, assists the patient in eliminating subsequent use of the anti-depressant drug.

18. The method of claim 17 wherein the second drug is quinidine.

19. The method of claim 17 wherein the second drug is selected from the group consisting of yohimbine, haloperidol, ajmaline, lobeline, and pipamperone, and salts and isomers thereof.

20. The method of claim 17 wherein the oxidase inhibitor drug is selected from the group consisting of labetalol, chlorpromazine, domperidone, quinine, oxprenolol, propranolol, timolol, metaprolol, diphenhydramine, papaverine, and mexiletine, and salts and isomers thereof.

* * * * *